United States Patent [19]
Boberg et al.

[11] Patent Number: 5,629,300
[45] Date of Patent: May 13, 1997

[54] DRUG CONTAINING (−)-METRIPHONATE

[75] Inventors: Michael Boberg; Wolfgang Kanhai; Armin Kern; Volker Muschalek, all of Wuppertal; Ulrich Pleiss, Wülfrath, all of Germany

[73] Assignee: Bayer Aktiengesellschaft, Leverkusen, Germany

[21] Appl. No.: 331,643

[22] PCT Filed: Dec. 9, 1993

[86] PCT No.: PCT/EP93/01228

§ 371 Date: Nov. 10, 1994

§ 102(e) Date: Nov. 10, 1994

[87] PCT Pub. No.: WO93/24130

PCT Pub. Date: Dec. 9, 1993

[30] Foreign Application Priority Data

May 26, 1992 [DE] Germany .............. 42 17 396.5

[51] Int. Cl.$^6$ .................................................. A61K 31/66
[52] U.S. Cl. ......................................................... 514/129
[58] Field of Search ................................... 514/129, 141

[56] References Cited

U.S. PATENT DOCUMENTS 4,950,658  8/1990  Becker et al. .................. 514/129

OTHER PUBLICATIONS

Keio Journal of Medicine, vol. 36, No. 4, (1987), E. Giacobini, pp. 381–391.

Drug Development Research, vol. 12, No. 3/4, (1988) R.E. Becker et al., pp. 163–195.

Clinical Pharmacokinetics, vol. 15, No. 2, (1988) G. Edwards et al, pp. 67–93.

Brienne et al., C.R. Hebd. Seances Acad. Sci. (1975), 280 (5), 291–2.

Primary Examiner—Phyllis G. Spivack
Attorney, Agent, or Firm—Sprung Horn Kramer & Woods

[57] ABSTRACT

A metrifonate-containing medicament is disclosed that contains the (−)-enantiomeric metrifonate as the sole active compound providing better cholinesterase-inhibition than the racemate.

10 Claims, No Drawings

DRUG CONTAINING (−)-METRIPHONATE

This application is a 371 of PCT/EP93/01228 filed Dec. 9, 1993.

The invention relates to medicaments which as the sole active compound contain the (−)-enantiomeric metrifonate, their preparation and their use.

O,O-Dimethyl 2,2,2-trichloro-1-hydroxyethyl-phosphonate of the formula

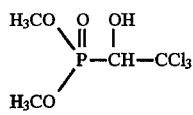

also known under the name metrifonate, is an insecticide which has been known for a long time.

Moreover, it is known that metrifonate has anthelmintic properties and can therefore be used for the treatment of disorders (such as, for example, bilharziasis) caused by certain worm types both in veterinary and human medicine.

U.S. Pat. No. 4,950,658 disclosed that both metrifonate itself and the 2,2-dichlorovinyl dimethyl phosphonate of the formula

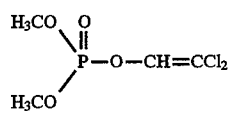

(also known as dichlorfon or DDVP) obtainable by elimination of hydrogen chloride from and rearrangement of metrifonate is suitable for the treatment of senile dementia, in particular of the Alzheimer's disease type, on account of its property of inhibiting cholinesterase.

Metrifonate has an asymmetric carbon atom and can thus exist in two enantiomers. Both when used as an insecticide and when used therapeutically, metrifonate is only employed as a racemate. As is known for many active compounds and here, in particular, for medicament active compounds, one enantiomeric form is frequently more active than the other enantiomeric form, and in individual cases the biological activity is really only to be attributed to one of the enantiomers.

Very little is known hitherto about the enantiomers of metrifonate. Utschik describes the existence of enantiomers of metrifonate in connection with crystal modifications, but without characterizing the enantiomers themselves [H. Utschik Z. Chem. 23 (8), 207 (1983) and Z. Chem. 29 (1), 26 (1989)].

In 1975, the enantiomers were purposely synthesized for the first time and investigated for their biological activity with respect to their cholinesterase-inhibiting properties in comparison to the racemate. The authors found that the enantiomers only differed negligibly from one another [J. Brienne et al., C. R. Hebd. Seances Acad. Sci. Ser. C 280 (5), 291–292 (1975)].

For this reason, until now no advantage was seen in using one of the enantiomers of metrifonate on its own instead of the racemate used hitherto.

Surprisingly, it has now been found that, contrary to the established opinion, according to which it is not an advantage to use a metrifonate enantiomer on its own, the (−)-form of metrifonate has a considerably greater pharmacological potential than was to be suspected.

It has been found that (−)-metrifonate has a considerably higher stability against active compound-degrading (metabolizing) enzymes than the (+)-enantiomer. For example, it was possible to show that, after reaction with human liver microsomes, there was up to 20 times more (−)-metrifonate available than (+)-metrifonate. When using (−)-metrifonate on its own as an active compound, a considerably better cholinesterase inhibition can thus be achieved than when using the racemate or the (+)-enantiomer.

When using (−)-metrifonate instead of the racemate to achieve the same action, it is possible to manage with considerably less active compound, even less than half, and the patients are considerably less stressed, in particular during continuous treatment.

Moreover, it is also advantageous that medicaments which only contain (−)-metrifonate have a smaller volume than the racemate-containing ones, which, for example, has a positive effect on the tablet size.

The metrifonate enantiomers can either be synthesized by the method given in the literature [J. Brienne et al., C. R. Hebd. Seances Acad. Sci. Ser. C 280 (5), 291–292 (1975)] or obtained from the racemate by resolution on a chiral adsorbent.

The invention relates to (−)-metrifonate-containing medicaments, pharmaceutical preparations for oral, parenteral or transdermal administration being understood among these, which besides the active compound (−)-metrifonate contain suitable auxiliaries and excipients. Examples which may be mentioned here are: tablets, coated tablets, pills or capsules, optionally in each case as the sustained-release form, suppositories, plasters or injection solutions.

The active compound (−)-metrifonate should be present in these preparations in a concentration of 0.1 to 99.5% by weight, preferably of 0.5 to 95% by weight of the total mixture.

The abovementioned pharmaceutical preparations can be prepared in a customary manner by known methods, for example using the auxiliary(ies) or excipient(s).

In general, it has proven advantageous to administer the active compound (−)-metrifonate in total amounts from about 0.01 to about 10 mg/kg, preferably in total amounts from about 0.1 mg/kg to 5 mg/kg, particularly preferably from 0.5 to 2.5 mg/kg of body weight every 24 hours, if appropriate in the form of several individual doses, to achieve the desired result.

However, it may optionally be advantageous to depart from the amounts mentioned, namely depending on the species and the body weight of the subject to be treated, on individual behaviour towards the medicament, the nature and severity of the disorder, the type of preparation and administration, and the time or interval at which administration takes place.

It is also possible to prepare sustained-release formulations for oral administration or to use transdermal application systems such as, for example, plasters.

| Example 1/tablets | |
|---|---|
| Metrifonate | 10.0 mg |
| Microcrystalline cellulose | 34.0 mg |
| Calcium phosphate | 20.0 mg |
| Sodium phosphate | 3.0 mg |
| Na carboxy-methylcellulose | 3.0 mg |
| Example 2/capsules | |
| Metrifonate | 10.0 mg |
| Avicel | 24.0 mg |

| | |
|---|---|
| Lactose | 55.0 mg |
| Maize starch | 10.0 mg |
| Aerosil | 0.5 mg |
| Mg stearate | 0.5 mg |
| Hard gelatin capsule size 5 | |

We claim:

1. A composition consisting of:
   (i) 0.1 to 99.5% by weight of (−)-metriphonate; and
   (ii) 99.9 to 0.5% by weight of a pharmaceutically acceptable auxiliary, a pharmaceutically acceptable excipient or a combination thereof;
   the total of (i)+(ii) being 100% by weight.

2. A composition according to claim 1, which is in a form suitable for oral administration.

3. A composition according to claim 1, which is in a form suitable for transdermal application.

4. A composition according to claim 1; which is in a sustained-release form.

5. A composition according to claim 1, which is in a form suitable for injection.

6. A method of treating senile dementia in a patient suffering therefrom comprising administering to said patient an amount of a composition which is effective to treat said senile dementia, said composition consisting of:
   i) 0.1 to 99.5% by weight of (−)-metriphonate; and
   (ii) 99.9 to 0.5% by weight of a pharmaceutically acceptable auxiliary, a pharmaceutically acceptable excipient or a combination thereof;
   the total of (i)+(ii) being 100% by weight.

7. The method according to claim 6, wherein said composition is in a form suitable for oral administration.

8. The method according to claim 6, wherein said composition is in a form suitable for transdermal application.

9. The method according to claim 6, wherein said composition is in a sustained-release form.

10. The method according to claim 6, wherein said composition is in a form suitable for injection.

* * * * *

UNITED STATES PATENT AND TRADEMARK OFFICE
CERTIFICATE OF CORRECTION

PATENT NO. : 5,629,300

DATED : May 13, 1997

INVENTOR(S) : Boberg, et al.

It is certified that error appears in the above-identified patent and that said Letters Patent is hereby corrected as shown below:

Title Page   [22] PCT Filed:  Delete " Dec. 9, 1993 " and substitute -- May 17, 1993 --

Signed and Sealed this

Eighteenth Day of November 1997

Attest:

BRUCE LEHMAN

Attesting Officer

Commissioner of Patents and Trademarks